US010835725B2

(12) United States Patent
Xiao

(10) Patent No.: US 10,835,725 B2
(45) Date of Patent: Nov. 17, 2020

(54) TATTOO NEEDLE TIP WITH CAPILLARY INK RESERVOIR AND COMBINED DEVICE THEREOF

(71) Applicant: Long Xiao, Guangdong (CN)

(72) Inventor: Long Xiao, Guangdong (CN)

(*) Notice: Subject to any disclaimer, the term of this patent is extended or adjusted under 35 U.S.C. 154(b) by 480 days.

(21) Appl. No.: 15/123,464

(22) PCT Filed: Apr. 7, 2015

(86) PCT No.: PCT/CN2015/075980
§ 371 (c)(1),
(2) Date: Sep. 2, 2016

(87) PCT Pub. No.: WO2015/154649
PCT Pub. Date: Oct. 15, 2015

(65) Prior Publication Data
US 2017/0072178 A1    Mar. 16, 2017

(30) Foreign Application Priority Data

Apr. 8, 2014 (CN) .................. 2014 2 0167938 U

(51) Int. Cl.
*A61M 37/00* (2006.01)

(52) U.S. Cl.
CPC .............................. *A61M 37/0084* (2013.01)

(58) Field of Classification Search
CPC .......... A61M 37/0076; A61M 37/0084; A61M 37/0092; A01K 11/005
See application file for complete search history.

(56) References Cited

U.S. PATENT DOCUMENTS

2013/0226211 A1    8/2013  Xiao

FOREIGN PATENT DOCUMENTS

| CN | 202538157 | * | 11/2012 | ............ A61M 37/00 |
|---|---|---|---|---|
| CN | 202538157 U | | 11/2012 | |
| CN | 203198469 U | | 9/2013 | |
| CN | 203898927 U | | 10/2014 | |

* cited by examiner

*Primary Examiner* — Todd J Scherbel
*Assistant Examiner* — Mikail A Mannan
(74) *Attorney, Agent, or Firm* — Laurence A. Greenberg; Werner H. Stemer; Ralph E. Locher

(57) ABSTRACT

A tattoo needle tip (10) with a capillary ink reservoir (13) and combined device thereof are provided. The tattoo needle tip (10) includes a needle tip body (11). A needle passage (100) is defined inside the needle tip body (11) for placing a tattoo needle (20). The needle opening (12) is communicated with the needle passage (100). A capillary disposed ink reservoir (13) directly connected to the needle opening (12) whereby can directly feed ink to the sharp end of the tattoo needle (20).

5 Claims, 5 Drawing Sheets

TATTOO NEEDLE TIP WITH CAPILLARY INK RESERVOIR AND COMBINED DEVICE THEREOF

BACKGROUND OF THE INVENTION

1. Field of the Invention

The present invention relates to an application device for tattooing or for making permanent make-up, particularly relates to a tattoo needle tip with a capillary ink reservoir and its combined devices with a handle and with a tattoo needle.

2. The Related Arts

A conventional tattoo device generally includes a tattoo machine, a handle, a needle tip and a tattoo needle. The user assembles these components together before use. While assembling, the handle is connected to the tattoo machine, the needle tip is placed on the handle, the tattoo needle passes through the central hole of the handle with the sharp end of the needle thereof reaching the opening of the tattoo needle tip.

In prior art, the basic shape of the needle tip is essentially a cylindrical tube. One end of the needle tip has a frustum section with a needle passage being defined therethrough. The free end of the frustum section is provided with a needle opening for the tattoo needle extending out.

The interior of the frustum section of the needle tip forms an inner cavity in a shape of a frustum. The inner cavity is communicated with the needle opening. The inner walls of the inner cavity and the needle opening are mostly designed to be streamlined and smooth, so as to prevent the sharp end of the needle from resisting when the tattoo needle is inserted thereby preventing the sharp end of the needle from bending. Meanwhile the inner cavity also serves as an ink reservoir.

During operation, the tattoo needle is doing a straight-line reciprocating motion in high frequency. The sharp end of the needle wetted by tattoo ink rushes out from the needle opening and stabs into the skin, then the sharp end of the needle returns into the needle opening for dipping some ink and then rushes out again. The section of the needle opening for feeding ink to the sharp end of the needle is the feed section. When adding ink to the needle tip, the tattooist inserts the needle tip into a small ink cup. There is a gap between the inner wall of the needle opening and the tattoo needle. Generally the ink will go into the needle opening and moisturize the needle opening and the inner wall of the needle passage. Some tattooists will briefly start the tattoo machine at the same time as dipping ink, then the tattoo needle does an up and down reciprocating motion in high speed, which will raise the ink to fill the inner cavity of the frustum section. In tattooing, the smooth inner wall of the inner cavity in the needle tip cannot effectively retain the ink. Therefore, the ink will flow to the needle opening due to the gravity and the motion of the tattoo needle.

The common issue met by tattooists when using these needle tips is that, if too much ink is added to the needle tip, it is easy to cause leakage of ink and pollute the tattoo during tattooing. In order to avoid the leakage of ink, tattooists have to add little ink each time, which increases the frequency of adding ink and results in ink failure or insufficient ink provision. However, it is inconvenient for tattooists to add ink frequently in tattooing. The frequent occurrence of ink failure or insufficient ink provision will adversely affect tattooists in drawing fluent and long tattoo lines.

U.S. Patent No. 20130226211 A1 and Chinese patent No. 202538157U disclose a needle tip with a capillary ink reservoir. The ink reservoir has functions of ink storage and ink maintenance, whereby once dipping ink, the tattoo needle tip can keep tattooing for a longer time. Thus tattooists can avoid dipping ink frequently when tattooing. The capillary ink reservoir is connected to the needle opening via an ink guide channel. There is a certain distance from the capillary ink reservoir to the needle opening. To quickly fill the capillary ink reservoir with ink, tattooists need to immerse the ink reservoir in the small ink cup with a deeper insertion when dipping ink. Since the deeper insertion leads to too much ink on the outside surface of the needle tip, tattooists have to constantly wipe off the ink on the outside surface of the needle tip. Due to the ink guide channel spaced between the ink reservoir and the needle opening, it is not easy to supply ink with poor mobility and high viscosity to the needle opening timely and sufficiently. There is a phenomenon that some amount of ink left in the capillary ink reservoir cannot flow to the needle opening, which results in the low efficiency of the capillary ink reservoir. The ink guide channel cannot adapt well to ink of different viscosities at the same time. For ink of low viscosity, a gap size of the ink guide channel shall be smaller, which will cause ink of high viscosity from failing to flow through the channel fluently. Thus, the gap size of the ink guide channel should be bigger for ink of high viscosity, which will cause flooding or leakage of ink of low viscosity.

SUMMARY OF THE INVENTION

An object of the present invention is to provide a tattoo needle tip with a capillary ink reservoir, which has functions of ink storage and ink maintenance, does not easily cause leakage of ink, and insures rapid filling of the ink reservoir, also insures effective feeding of the ink to the sharp end of the tattoo needle during tattooing.

Another object of the present invention is to provide a combined device comprising a tattoo needle tip with a capillary ink reservoir and a handle, which forms a combined component of a tattoo device, has functions of ink storage and ink maintenance, does not easily cause leakage of ink, and insures rapid filling of the reservoir, also insures effective feeding of the ink to the sharp end of the tattoo needle during tattooing.

A further object of the invention is to provide a combined device comprising a tattoo needle tip with a capillary ink reservoir and a tattoo needle, which forms a combined component of a tattoo device, has functions of ink storage and ink maintenance, does not easily cause leakage of ink, and insures rapid filling of the reservoir, also insures effective feeding of the ink to the sharp end of the tattoo needle during tattooing.

To achieve the above objects, a tattoo needle tip with a capillary ink reservoir of the present invention includes a needle tip body. A needle passage is defined inside the needle tip body for placing a tattoo needle. A needle opening is defined at one end of the needle tip body for the sharp end of the tattoo needle to extend out. The needle opening is communicated with the needle passage. A capillary ink reservoir adapted to receive and retain ink therein by capillary action is disposed on the needle tip body and directly connected to the needle opening whereby the ink reservoir can directly feed ink to the sharp end of the tattoo needle.

Wherein a plurality of capillary ink containing bodies are provided at the ink reservoir and are directly connected to the needle opening.

Wherein each ink containing body is a capillary aperture defined in the ink reservoir.

All the capillary apertures defined in the ink reservoir are connected to the needle opening directly.

Wherein the ink reservoir is made of porous material or fibrous material, and the ink containing body is a pore in the ink reservoir or a gap between fibers.

Wherein the ink reservoir is integrally or detachably formed at the needle tip body.

A combined device of the present invention includes a handle and a tattoo needle tip with a capillary ink reservoir installed to the handle. The tattoo needle tip includes a needle tip body. A needle passage is defined inside the needle tip body for placing a tattoo needle. A needle opening is defined at one end of the needle tip body for the sharp end of the tattoo needle to extend out. The needle opening is communicated with the needle passage. A capillary ink reservoir adapted to receive and retain ink therein by capillary action is disposed on the needle tip body and directly connected to the needle opening whereby the ink reservoir can directly feed ink to the sharp end of the needle.

A combined device in accordance with a further embodiment of the present invention includes a tattoo needle tip with a capillary ink reservoir and a tattoo needle installed therein. The tattoo needle tip includes a needle tip body. A needle passage is defined inside the needle tip body for placing the tattoo needle. A needle opening is defined at one end of the needle tip body for the sharp end of the tattoo needle to extend out. The needle opening is communicated with the needle passage. A capillary ink reservoir adapted to receive and retain ink therein by capillary action is disposed on the needle tip body and directly connected to the needle opening whereby the ink reservoir can directly feed ink to the sharp end of the needle.

Wherein a plurality of capillary ink containing bodies are provided at the ink reservoir and are directly connected to the needle opening.

Wherein each ink containing body is a capillary aperture defined in the ink reservoir.

Wherein all the capillary apertures defined in the ink reservoir are connected to the needle opening directly.

Wherein the ink reservoir is made of porous material or fibrous material, and the ink containing body is a pore in the ink reservoir or a gap between fibers.

Wherein the ink reservoir is integrally or detachably formed at the needle tip body.

In summary, by locating the ink reservoir at the needle tip, the present invention utilizes the capillary principle to store ink in the ink reservoir, which can store and retain a great amount of ink. Therefore, the leakage of ink does not easily happen. The ink containing body of the ink reservoir is connected to the needle opening directly, and the sharp end of the needle continuously dips the ink in the needle opening via the reciprocating motion of the tattoo needle, realizing that dipping and adding ink once, the tattoo needle tip keeps tattooing for a longer time, so as to avoid dipping and adding ink frequently when tattooists are tattooing. Moreover, it is quick and easy to dip and add ink to the ink reservoir.

For further explaining the technical solution and the effect of the present invention, the object, the characteristic and the feature of the present invention are best understood from the following detailed description with reference to the accompanying figures, but the figures are only for reference and explaining, not to limit the scope of the invention.

BRIEF DESCRIPTION OF THE DRAWINGS

The technical solution and the beneficial effects of the present invention are best understood from the following detailed description with reference to the accompanying figures and embodiments.

In the figures.

DETAILED DESCRIPTION OF THE PREFERRED EMBODIMENTS

Figure 1:
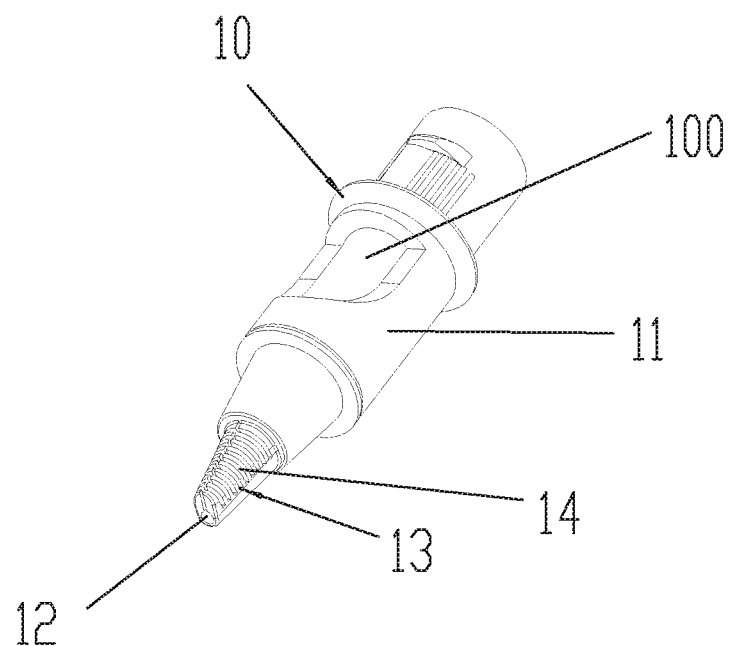
FIG. 1 is a perspective view of a tattoo needle tip with a capillary ink reservoir according to one embodiment of the present invention.
Figure 2:
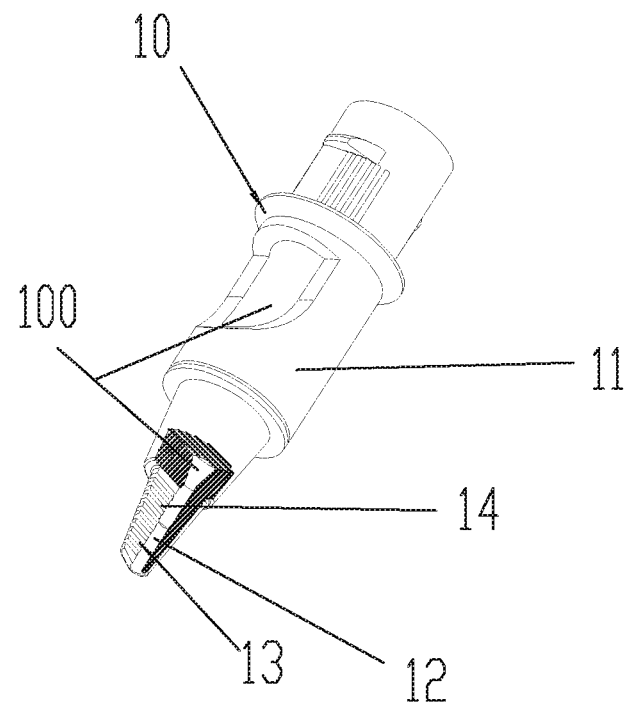
FIG. 2 is a partial section view of FIG. 1.

As shown in FIGS. 1-2, a tattoo needle tip 10 with a capillary ink reservoir according to one embodiment of the present invention includes a needle tip body 11. A needle passage 100 is provided through the needle tip body 11 for placing a tattoo needle 20 (see FIG. 7). A needle opening 12 is provided at one end of the needle tip body 11. The needle opening 12 is a hole extending through the end wall of the needle tip body 11. The needle opening 12 is communicated with the needle passage 100. The sharp end 211 (see FIG. 8) of the tattoo needle can extend out from the needle opening 12. One capillary ink reservoir 13 is provided on the needle tip body 11 for maintaining and storing ink. The capillary ink reservoir 13 has at least one capillary ink containing body 14. The ink for tattooing can be maintained and stored in the capillary ink containing body 14 of the capillary ink reservoir 13 by capillary action. The capillary ink reservoir 13 is adjacent to the needle opening 12. The ink in the ink containing body 14 flows to the needle opening 12 directly and feeds to the sharp end 211 (see FIG. 9) of the tattoo needle.

The ink reservoir 13 is integrally or detachably formed at the needle tip body 11. The ink containing body 14 may be a plurality of capillary apertures. The gap in the capillary apertures is a capillary gap, whereby the ink reservoir 13 can be used to absorb and retain ink by capillarity. The ink reservoir 13 may be formed of porous material, and the ink containing body 14 is a capillary pore in the ink reservoir 13 and has the function of capillarity. Alternatively, the ink reservoir 13 is formed of fibrous material, such as a plurality of fibers, and the gap between the fibers in the ink reservoir 13 forms the ink containing body 14 and is a capillary gap with the function of capillarity. Compared with the conventional cavity with smooth inner wall, the present invention utilizes the aforesaid capillary ink reservoir 13 to store and supply ink, which can store a great amount of ink, and does not easily cause leakage of ink. The ink reservoir 13 is located to be adjacent to the needle opening 12 with a plurality of ink containing bodies 14 being formed at the wall of the needle opening 12. The ink in the ink containing body 14 flows to the needle opening 12 directly, without a special ink guide channel between the ink containing body 14 and the needle opening 12 of the prior art. Compared with U.S. patent No. 20130226211 A1 and Chinese patent No. 202538157U, the present invention prevents the phenomenon of nonfluency when ink with poor mobility and high viscosity passes through the ink guide channel. The present invention can supply ink to the needle opening timely and sufficiently, whereby tattooists do not have to insert the needle tip into the ink cup deeply as Chinese patent No. 202538157U does for immersing the ink containing body when dipping ink. Ink with poor mobility and high viscosity is directly immersed to supply the ink containing body without passing through the ink guide channel, when tattooists are dipping ink. Thus, the present invention realizes to dip and add ink quickly and easily.

The ink reservoir 13 and the needle tip body 11 can be integrated and manufactured as one piece and connected thereon, or can be manufactured separately, then connected together.

As shown in FIGS. 1-2, in the embodiment, the needle opening 12 is in the shape of a hole, the ink reservoir 13 is adjacent to the needle opening 12, the ink containing body 14 is a capillary slot directly formed in the wall of the needle opening 12, and the ink in the ink containing body 14 flows to the needle opening 12 directly.

Figure 3:
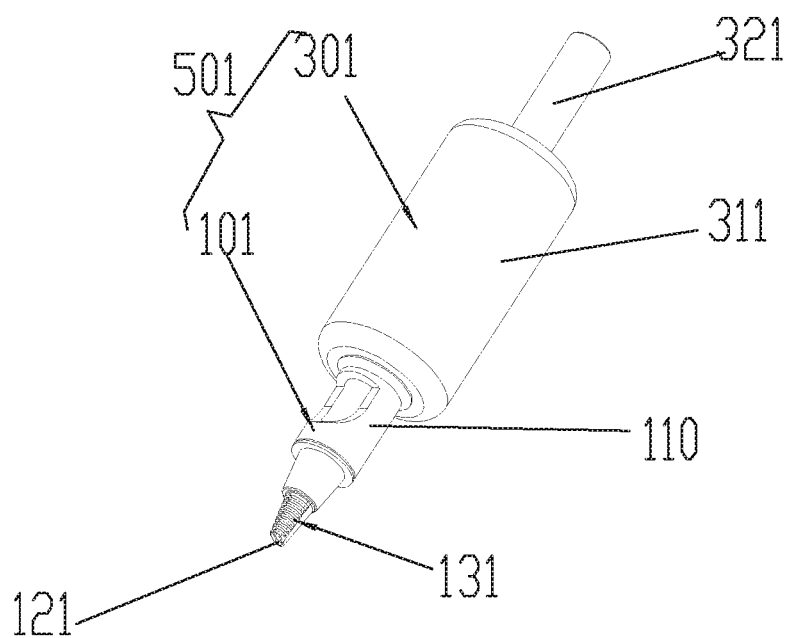
FIG. 3 is a perspective view of a combined device including a tattoo needle tip with a capillary ink reservoir and a handle according to one embodiment of the present invention.

Please refer to FIG. 3, a combined device 501 according to the present invention includes a handle 301 and a tattoo needle tip 101 assembled to the handle 301. The structure of the tattoo needle tip 101 is similar to the abovementioned tattoo needle tip 10 with the capillary ink reservoir. In the embodiment shown in FIG. 3, the handle 301 and the tattoo needle tip 101 with the capillary ink reservoir are integrated and manufactured as one piece. The combined device forms a combined component of a tattoo device, tattooists can install a tattoo needle on the combined device, and then install them to a tattoo machine for use.

As shown in FIGS. 1-3, the tattoo needle tip 101 with the capillary ink reservoir is connected to the handle 301 integrally. The handle 301 includes a holding body 311 and a handle neck 321 located at one end of the holding body 311. One end of the needle tip body 110 distant from the needle opening 121 is integrally connected with the other end of the holding body 311. Furthermore, the tattoo needle tip 101 includes the ink reservoir 131 having the ink containing body for maintaining and storing ink. A guide hole (not shown) is defined in the handle 301. The guide hole extends through the handle neck 321 and the interior of the holding body 311 successively, and is in communication with the needle passage inside the tattoo needle tip 101.

Figure 4:
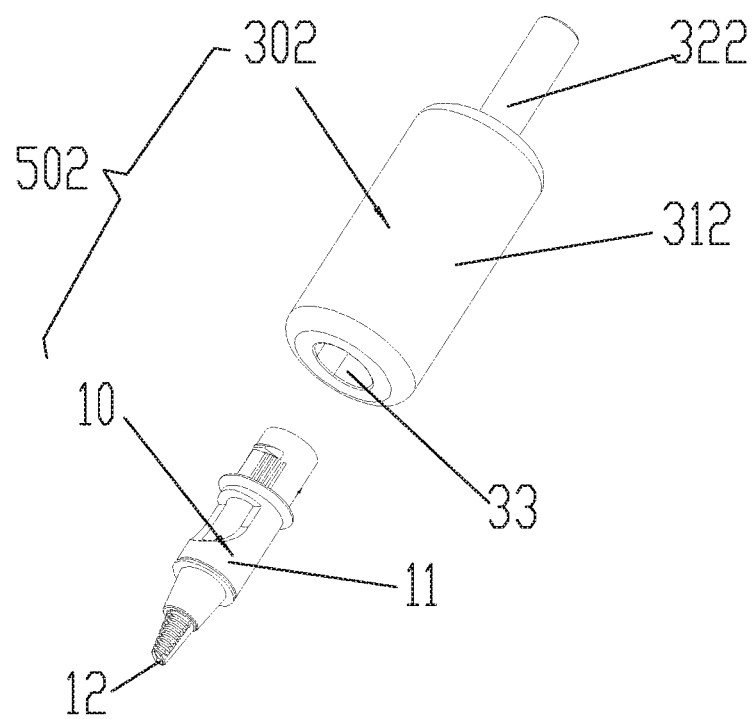
FIG. 4 is a perspective view of a combined device including a tattoo needle tip with a capillary ink reservoir and a handle according to another embodiment of the present invention.
Figure 5:
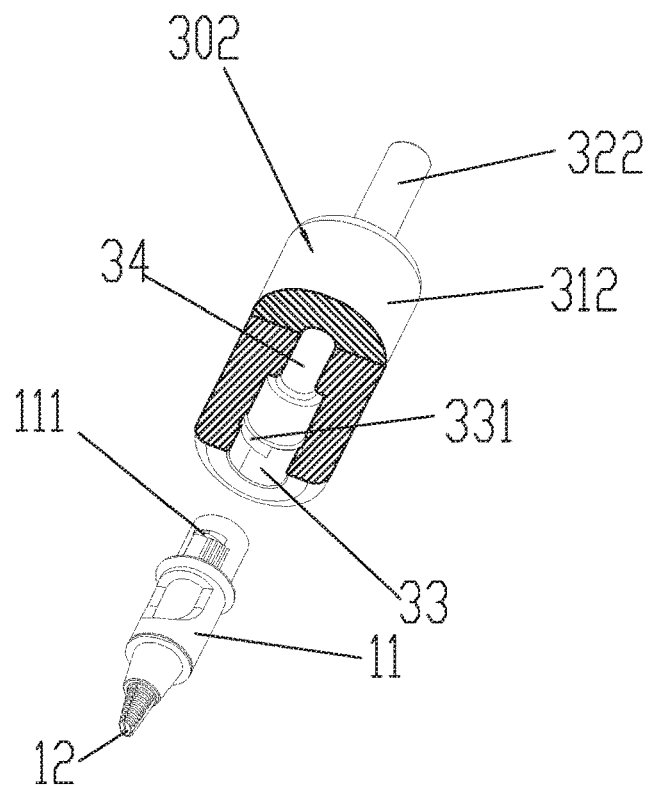
FIG. 5 is a partial section view of FIG. 4.

As shown in FIGS. 4-5, in combination with FIGS. 1-2, a combined device 502 according to another embodiment of the present invention is shown. A tattoo needle tip 10 with the capillary ink reservoir is installed at the handle 302 detachably. The handle 302 includes a holding body 312, a handle neck 322 located at one end of the holding body 312, and a needle tip installation portion 33 located at the other end of the holding body 312. A guide hole 34 is defined to extend through the handle neck 322 and the holding body 312 successively, thereafter to communicate with the needle tip installation portion 33. The tattoo needle tip 10 with the capillary ink reservoir can be detachably installed to the needle tip installation portion 33. In the embodiment, the needle tip installation portion 33 is located in the guide hole at one end of the holding body 312. The needle tip installation portion 33 has a containing slot 331. Corresponding to the containing slot 331, a snap-fit portion 111 is positioned on the outside of one end of the needle tip body 11 distant from the needle opening 12. The snap-fit portion 111 of the needle tip body 11 is snap-fitted in the containing slot 331, which forms a detachable locking mechanism of snap-fit style, so as to install the tattoo needle tip 10 to the handle 302 detachably. The needle tip body 11 and the needle tip installation portion 33 also can be installed by means of engagement of an axis and a hole, and so on. Instead of changing the handle, the detachable installation between the tattoo needle tip 10 and the handle 302 is convenient for tattooists to change tattoo needles of different specifications and needle tips adapted for tattoo needles of different specifications when tattooing.

Figure 6:
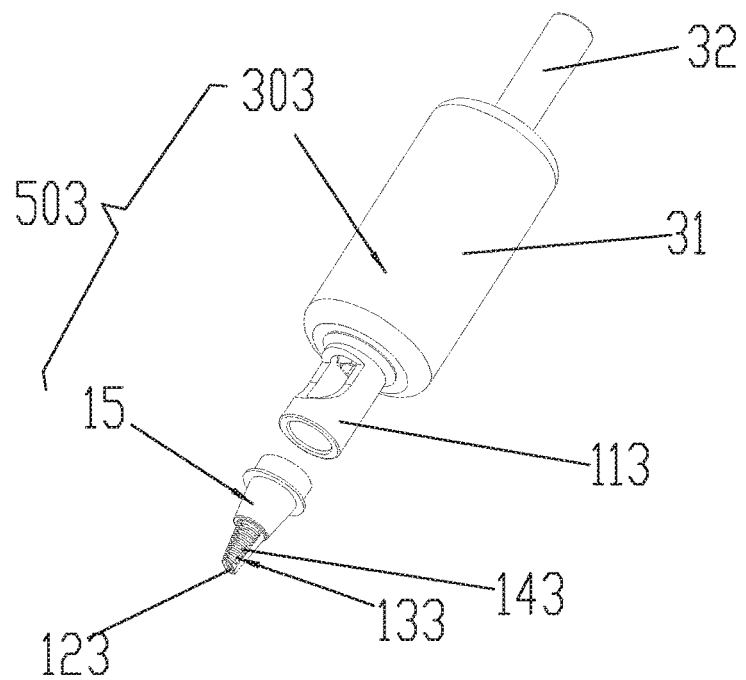
FIG. 6 is a perspective view of a combined device including a tattoo needle tip with a capillary ink reservoir and a handle according to a further embodiment of the present invention.

Referring to FIG. 6, a combined device 503 according to a further embodiment of the present invention includes a needle tip casing 15 and the handle 303. The needle tip casing 15 is installed to the handle 303 detachably. Meanwhile, in combination with FIGS. 1-2, the structure of the needle tip casing 15 and the handle 303 can be understood. In FIGS. 1-2, the capillary ink reservoir 13 and the tattoo needle opening 12 are integrated and manufactured as one piece, which forms the needle tip casing 15 shown in FIG. 6. Similar to the structure shown in FIGS. 1-2, the needle tip casing 15 includes an ink reservoir 133 for maintaining and storing ink. At least one capillary ink containing body 143 is provided in the ink reservoir 133. The ink for tattooing can be maintained and stored in the ink containing body 143 of the ink reservoir 133, and the ink reservoir 133 is adjacent to the needle opening 123. The needle tip casing 15 is detachably installed to the needle tip body 113, and the needle tip body 113 may be integrally or detachably connected to the handle 303. The structure of the needle tip body 113 can be with reference to the needle tip body 11 shown in FIGS. 1-2. Users may install needle tip casings 15 adapted for tattoo needles of different specifications.

Figure 7:
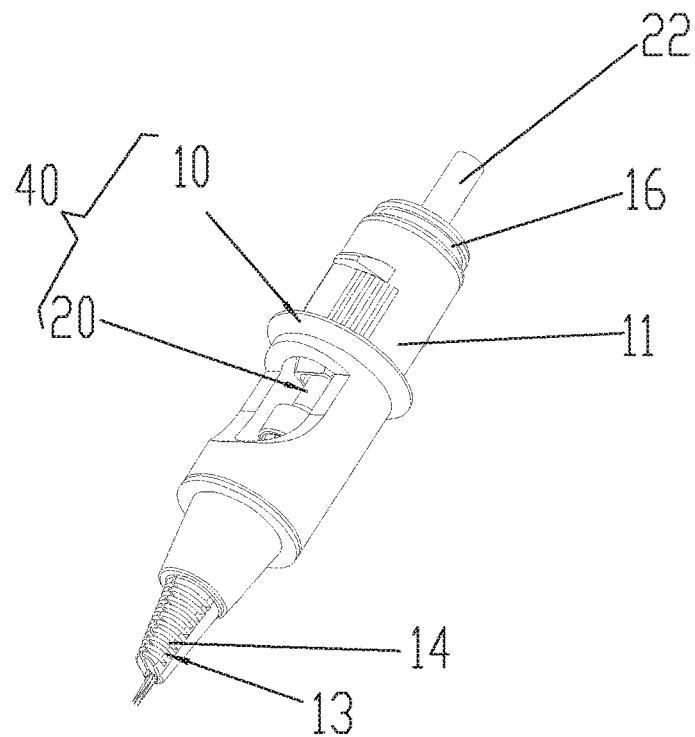
FIG. 7 is a perspective view of a combined device including a tattoo needle tip with a capillary ink reservoir and a tattoo needle according to one embodiment of the present invention.
Figure 8:
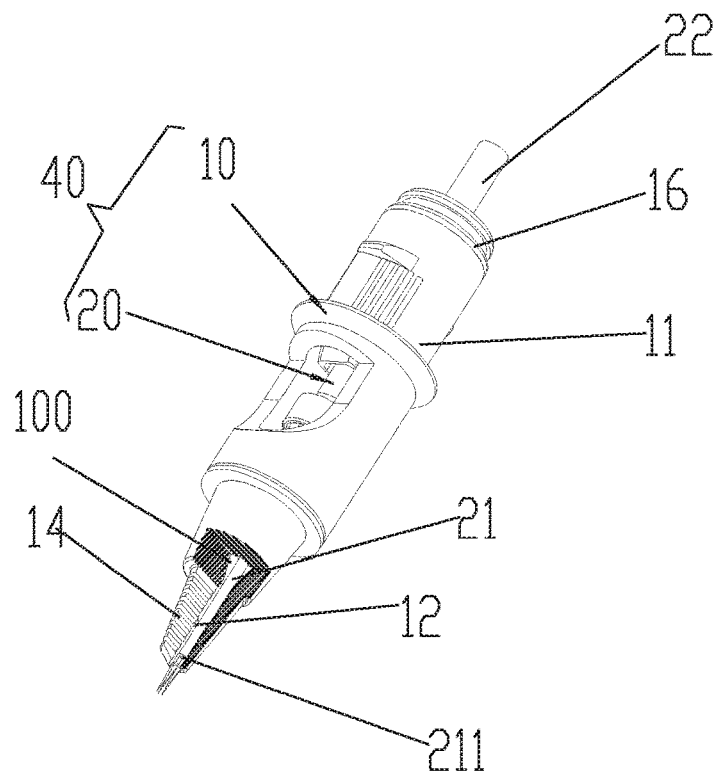
FIG. 8 is a partial section view of FIG. 7.

As shown in FIGS. 7-8, in combination with FIGS. 1-2, a combined device 40 in accordance with a further embodiment of the present invention includes a tattoo needle tip 10 and a tattoo needle 20 installed in the tattoo needle tip 10.

As shown in FIGS. 1-2, the tattoo needle tip 10 includes a needle tip body 11. A needle passage 100 is defined inside the needle tip body 11. A needle opening 12 is defined at one end of the needle tip body 11 and extends through the end wall of the needle tip body 11. The needle opening 12 is communicated with the needle passage 100. An ink reservoir 13 is provided on the needle tip body 11 for maintaining and storing ink. At least one capillary ink containing body 14 is provided on the ink reservoir 13. The tattoo needle 20 includes a needle head 21 and a needle bar 22 connected with the needle head 21. Most of the tattoo needle 20 is contained in the needle passage 100 of the needle tip body 11, and the sharp end 211 of the needle head 21 is located in the needle opening 12 when the sharp end 211 dips ink. In order to connect to an element driving the tattoo needle 20, the needle bar 22 extends out of the needle passage 100 from one end of the needle tip body 11 distant from the needle opening 12. The ink for tattooing can be maintained and stored in the ink containing body 14 of the ink reservoir 13, and the ink reservoir 13 is adjacent to the needle opening 12. A plurality of ink containing bodies 14 are formed in the wall of the needle opening 12. The ink in the ink containing body 14 will directly flow to the needle opening 12 for feeding the sharp end 211 of the tattoo needle 20 to continue tattooing.

In the embodiment, the other end of the needle tip body 11 opposite to the needle opening 12 is an open end. Furthermore, a cover 16 is covered on the open end. A hole is defined in the cover 16 for the needle bar 22 of the tattoo needle 20 to extend out.

Figure 9:
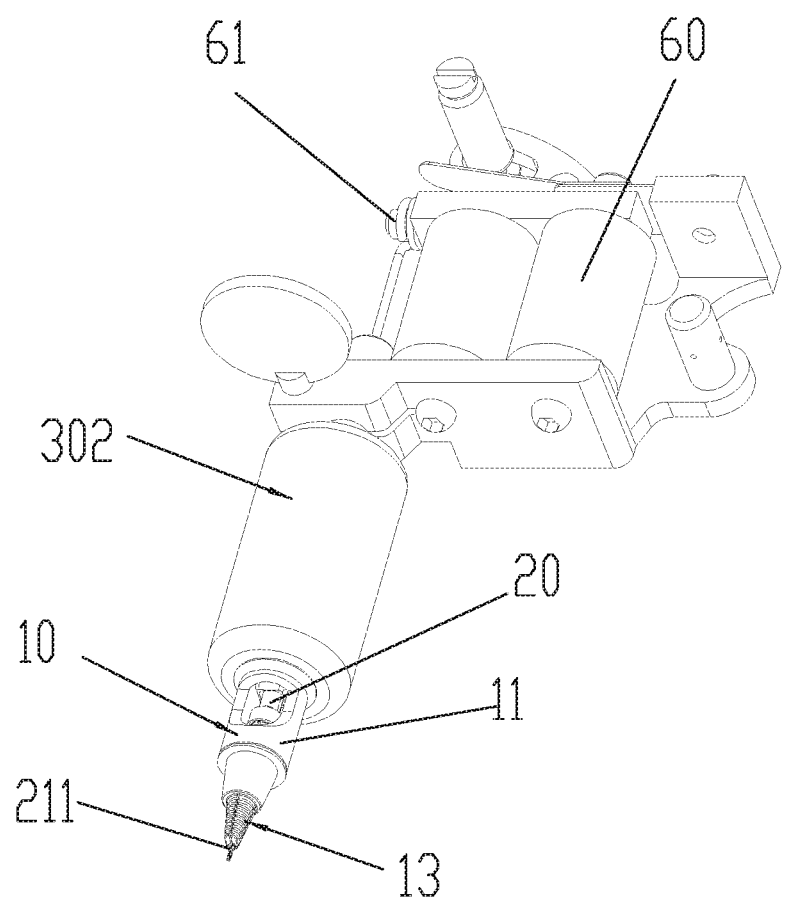
FIG. 9 is a perspective view of a combined device including a tattoo needle tip with a capillary ink reservoir, a handle, a tattoo needle and a tattoo machine according to the present invention.

Referring to FIG. 9, and combining with FIGS. 1-8, a combined device according to a further embodiment of the present invention includes a tattoo needle tip 10, a handle 302, a tattoo needle 20 and a tattoo machine 60. When in use, assemble the aforesaid tattoo needle tip 10 with the capillary ink reservoir, the tattoo needle 20 and the handle 302 together, connect the handle 302 to the tattoo machine 60, and insert the needle bar 22 of the tattoo needle 20 into the guide hole of the handle 302 to connect to a driving element 61 connected to the tattoo machine 60. Under the driving of the tattoo machine 60, the driving element 61 drives the tattoo needle 20 to do a straight-line reciprocating motion in high frequency in the tattoo needle tip 10, therefore, tattooists control the tattooing of the tattoo needle 20 by holding the handle 302. The capillary ink reservoir 13 of the tattoo needle tip 10 is adjacent to the needle opening 12, and the ink containing body 14 of the ink reservoir 13 is connected to the needle opening 12 directly. During operation, the tattoo needle 20 is doing a straight-line reciprocating motion in high frequency. The sharp end 211 of the needle wetted by ink rushes out from the needle opening 12 and stabs into the skin, then the sharp end 211 of the needle returns into the needle opening 12 and rushes out again with dipped ink. When adding ink, the tattoo needle tip 10 is inserted into a small ink cup, so that the ink immerses and fills the ink containing body 14 of the ink reservoir 13. When tattooing, the ink in the needle opening 12 is continuously dipped by the sharp end 211 of the needle head 21 of the tattoo needle 20 and enters into the skin. The ink in the ink containing body 14 will be directly supplied to the needle opening 12 due to the capillary force and the motion of the tattoo needle 20. The ink stored in the tattoo needle tip 10 by dipping and adding ink once can feed to the sharp end 211 of the tattoo needle 20 for many times of dipping. As a result, tattooists can avoid dipping ink frequently when tattooing. Moreover, it is quick and easy to dip and add ink.

In summary, by locating the ink reservoir at the needle tip, the present invention utilizes the capillary principle to store ink in the ink reservoir, which can store and retain a great amount of ink. Therefore, the leakage of ink is not easy to happen. The ink containing body of the ink reservoir is connected to the needle opening directly, and the sharp end of the needle continuously dips the ink in the needle opening via the reciprocating motion of the tattoo needle, realizing that dipping and adding ink once, the tattoo needle tip keeps tattooing for a longer time, so as to avoid dipping and adding ink frequently when tattooists are tattooing. Moreover, it is quick and easy to dip and add ink to the ink reservoir.

Above are only specific embodiments of the present invention, the scope of the present invention is not limited to this, and to any persons who are skilled in the art, change or replacement which is easily derived should be covered by the protected scope of the present invention. Thus, the protected scope of the present invention should go by the subject claims.

What is claimed is:

1. A combined device comprising a tattoo needle tip with a capillary ink reservoir and a tattoo needle installed therein, the tattoo needle tip including:
    a needle tip body;
    a needle passage being defined inside the needle tip body for placing the tattoo needle;
    a needle opening being defined at one end of the needle tip body for a sharp end of the tattoo needle to extend out, the needle opening being communicated with the needle passage; the capillary ink reservoir receiving and retaining ink therein by capillary action being disposed on the needle tip body and directly connected to the needle opening, the ink reservoir directly feeding ink to the sharp end of the needle; and
    a plurality of capillary ink containing bodies are provided at the ink reservoir and are directly connected to the needle opening.

2. The combined device of claim 1, wherein each ink containing body is a capillary aperture defined in the ink reservoir.

3. The combined device of claim 2, wherein all the capillary apertures defined in the ink reservoir are connected to the needle opening directly.

4. The combined device of claim 1, wherein a capillary ink containing body is provided at the ink reservoir and is directly connected to the needle opening, the ink reservoir is made of porous material or fibrous material, and the ink containing body is a pore in the ink reservoir or a gap between fibers.

5. The combined device of claim 1, wherein the needle opening has a wall and the ink reservoir has an ink containing body formed in the wall for directly supplying ink to the needle opening.

* * * * *